United States Patent [19]

Fortune et al.

[11] Patent Number: 5,507,279
[45] Date of Patent: Apr. 16, 1996

[54] RETROGRADE ENDOTRACHEAL INTUBATION KIT

[76] Inventors: John B. Fortune, 6162 E. Alta Vista, Tucson, Ariz. 85715; W. Brooks Fortune, 7933 Beaumont Green, West Dr., Indianapolis, Ind. 46250

[21] Appl. No.: 159,672

[22] Filed: Nov. 30, 1993

[51] Int. Cl.$^6$ ............................................. A61M 16/00
[52] U.S. Cl. ............................ 128/200.26; 128/207.14; 128/207.29
[58] Field of Search .................... 128/200.26, 207.14, 128/207.15, 207.29

[56] References Cited

U.S. PATENT DOCUMENTS

| | | | |
|---|---|---|---|
| 2,116,083 | 5/1938 | Rüsch | 451/55 |
| 2,463,149 | 3/1949 | Caine | 128/200.26 |
| 2,862,498 | 12/1958 | Weeks | 128/207.14 |
| 3,754,554 | 8/1973 | Felbarg | 128/200.26 |
| 4,405,314 | 9/1983 | Cope | 128/207.14 |
| 4,471,778 | 9/1984 | Toye | 128/207.29 |
| 4,488,545 | 12/1984 | Shen | 128/207.29 |
| 4,520,810 | 6/1985 | Weiss | 128/207.29 |
| 4,573,576 | 3/1986 | Krol | 206/471 |
| 4,586,505 | 5/1986 | Sisson et al. | 128/207.29 |
| 4,593,687 | 6/1986 | Gray et al. | 128/200.26 |
| 4,677,978 | 7/1987 | Melker | 128/207.14 |
| 4,898,163 | 2/1990 | George | 128/200.26 |
| 4,913,139 | 4/1990 | Ballew | 128/207.14 |
| 4,938,746 | 7/1990 | Etheredge, III et al. | 128/200.26 |
| 5,055,107 | 10/1991 | Lester | 128/207.29 |
| 5,058,577 | 10/1991 | Six | 128/200.26 |
| 5,058,580 | 10/1991 | Hazard | 128/207.15 |
| 5,186,168 | 2/1993 | Spofford et al. | 128/207.14 |
| 5,215,526 | 6/1993 | Deniega et al. | 604/164 |
| 5,217,005 | 6/1993 | Weinstein | 128/207.29 |
| 5,217,007 | 6/1993 | Ciaglia | 128/207.29 |

FOREIGN PATENT DOCUMENTS

| | | | |
|---|---|---|---|
| 284596 | 11/1990 | Germany | 128/207.29 |
| 9001350 | 2/1990 | WIPO | 128/207.29 |

Primary Examiner—Aaron J. Lewis
Attorney, Agent, or Firm—Schmeiser, Olsen & Watts

[57] ABSTRACT

A kit for performing a retrograde endotracheal intubation procedure including a tracheal puncture device for puncturing the trachea of a patient, and for facilitating the subsequent passage of an attached guide-wire into and through the trachea, and an endotracheal tube, having a modified beveled end portion including a supplementary guide hole adapted to receive the guide-wire, for expediting the passage of the endotracheal tube through the anatomical structures of the larynx.

10 Claims, 5 Drawing Sheets

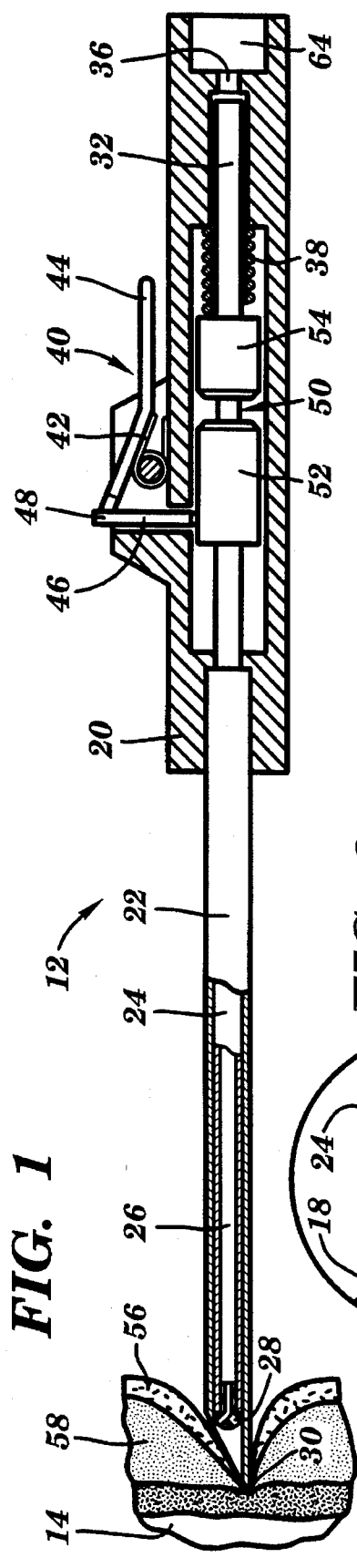
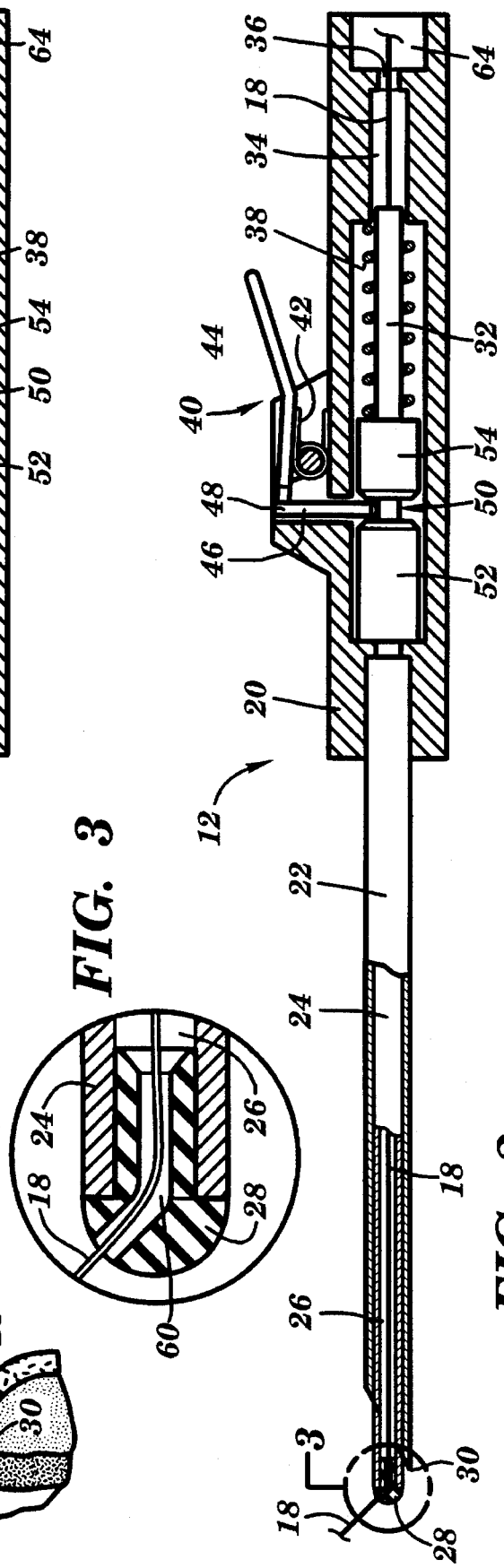

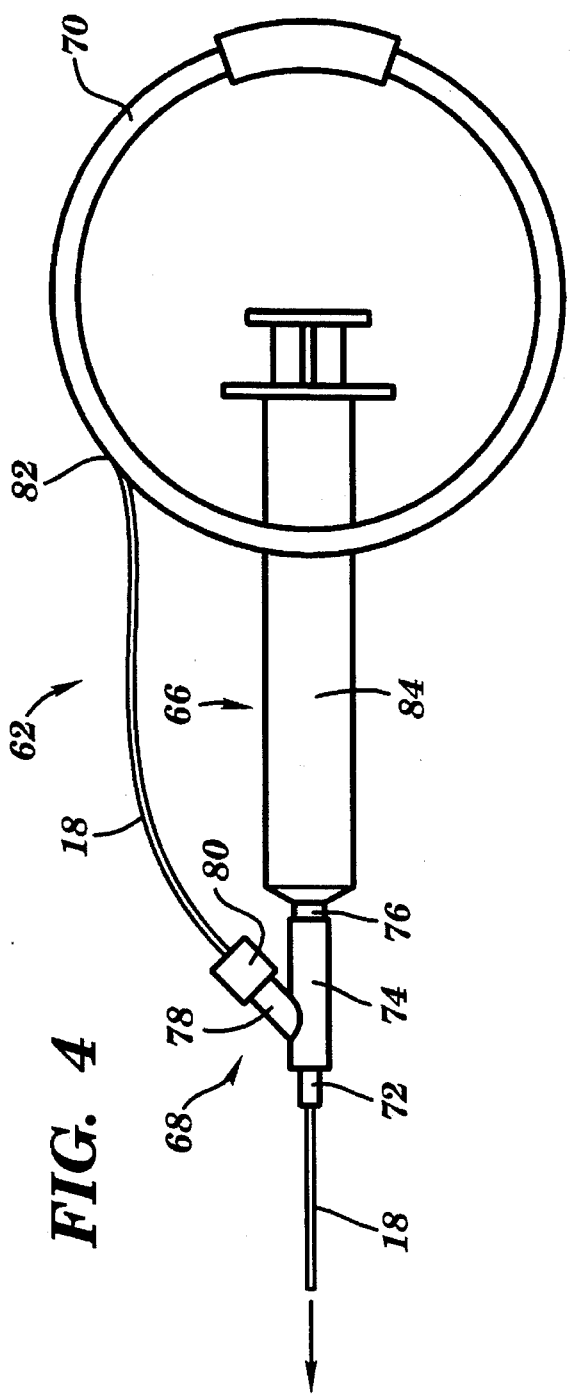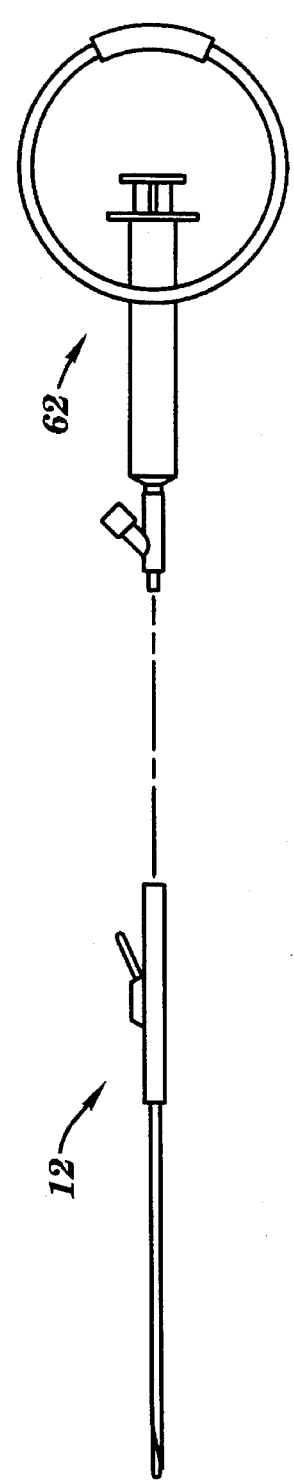
FIG. 4
FIG. 5

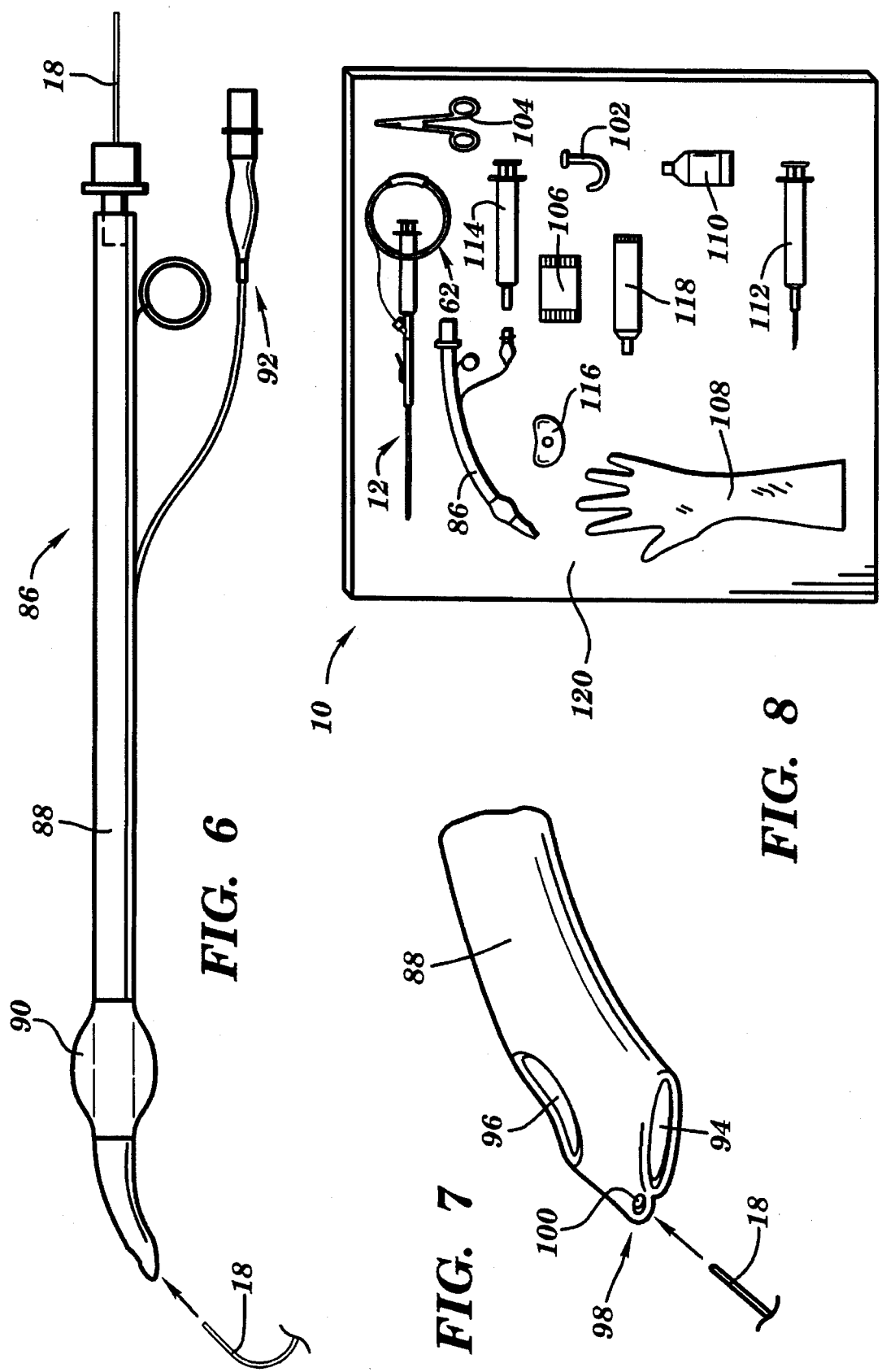

RETROGRADE ENDOTRACHEAL INTUBATION KIT

FIELD OF THE INVENTION

The present invention relates to surgical equipment and, more particularly, to a surgical kit for performing a retrograde wire-guided endotracheal intubation procedure in a safe and expeditious manner.

BACKGROUND OF THE INVENTION

As known in the art, the establishment of an adequate airway is oftentimes an essential initial step in the treatment of a patient suffering from a wide variety of diseases or injuries. Generally, the airway is established through an endotracheal intubation procedure, wherein an endotracheal tube is orally or nasally directed into the trachea of the patient. Most commonly, endotracheal intubation is performed with the aid of an ancillary laryngoscope, through which the vocal cords of the patient are directly illuminated and visualized during the tracheal insertion of an endotracheal tube. Unfortunately, conventional orolaryngeal endotracheal intubation is not always possible due to anatomical deviations, trauma to the airway and face, excessive blood and secretions, fractures to the cervical spine, or occlusions of the airway. In such cases, other intubation techniques, such as retrograde intubation or the like, may be utilized to provide a patient with a potentially lifesaving airway.

Retrograde intubation of the trachea, commonly designated as the Seldinger technique, involves the passage of a guide-wire through the trachea of a patient. More specifically, the guide-wire is threaded through a needle puncture site disposed proximate the cricothyroid membrane or cricoid plate of the larynx, and exits through the mouth or nose of the patient after passing through the vocal cords. The distal end of the guide-wire is subsequently passed through the lumen of a conventional plastic endotracheal tube. Using the wire as a guide, the endotracheal tube is directed into the mouth or nose, through the pharynx and vocal cords, and into the trachea of a patient. Thereafter, the guide-wire is removed and the endotracheal tube is secured within the trachea. Unfortunately, although this technique provides an effective alternative for conventional endotracheal intubation procedures, it suffers from several disadvantages.

In order to initiate the procedure, the trachea must be externally punctured with a hollow needle. As known in the art, the initial puncture of the trachea through the cricothyroid membrane requires a substantial amount of pressure. If sufficient care is not taken after the needle has successfully passed through the anterior wall of the trachea, the needle may inadvertently puncture the posterior wall of the trachea, potentially injuring the esophagus, carotid artery, jugular veins, or multiple other nearby organs.

Heretofore, retrograde wire-guided endotracheal intubation has been performed by passing a guide-wire into the lumen of an endotracheal tube through the main beveled end hole thereof, or through an aperture (the "Murphy's eye") disposed on the side wall of the tube. Unfortunately, due to the large amount of "play" afforded by the relatively large diameters of the main beveled end hole and Murphy's eye, the endotracheal tube generally becomes snagged on the epiglottis or vocal cords of a patient during a retrograde endotracheal intubation procedure, oftentimes resulting in local tissue trauma and/or delayed tube insertion.

Finally, retrograde intubation is commonly utilized in emergency situations when other intubation techniques for gaining airway access are unsuccessful or inappropriate. Unfortunately, the performance of this procedure requires the utilization of a variety of devices which are currently not packaged together in the form of a kit. Consequently, when it becomes apparent that retrograde endotracheal intubation is warranted in an emergency situation, there is often insufficient time available to gather the necessary equipment. As such, the establishment of an airway may be adversely delayed, potentially resulting in the death of a patient.

SUMMARY OF THE INVENTION

In order to avoid the disadvantages of the prior art, the present invention provides a kit for performing a retrograde wire-guided endotracheal intubation procedure. Advantageously, the retrograde endotracheal intubation kit includes an improved tracheal puncture device for externally puncturing a patient's trachea without injuring adjoining tissues or organs, and an improved endotracheal tube for expediting the downward passage of the endotracheal tube through the anatomical structures disposed in the back of pharynx and larynx, without the local tissue trauma commonly associated with prior art endotracheal tube designs.

The tracheal puncture device of the present invention includes a hub and a hollow needle. The hollow needle encloses a movable, hollow stem having a longitudinally extending inner channel therein, an apertured blunt end section which is adapted to movably protrude past the sharp edges of the needle point, and an opposing end section which communicates with an opening in the posterior of the needle hub. The needle hub contains a first biasing spring for continuously biasing the blunt end section of the hollow stem toward the apex of the hollow needle, and a spring biased, lever actuated locking mechanism for locking the blunt end section of the hollow stem in a position slightly beyond the sharp edges of the needle point. When the lever actuated locking mechanism is manually depressed, thereby compressing a second biasing spring, the hollow stem is allowed to move within the hollow needle under control of the first biasing spring. Upon release of the lever actuated locking mechanism, a cantilevered arm engages a corresponding detent on the hollow stem, thereby locking the hollow stem in the above-described position.

The hub of the tracheal puncture device is removably secured to a novel guide-wire carrier/aspirating syringe arrangement. More specifically, the guide-wire carrier/aspirating syringe arrangement includes a hollow Y-shaped plastic extension which is designed to communicate with the inner channel of the movable, hollow stem within the tracheal puncture device. The hollow Y-shaped plastic extension includes a base portion for removably coupling the extension to the hub of the tracheal puncture device, a first leg for removably receiving an aspirating syringe, and a second leg for receiving a guide-wire therethrough. In operation, the guide-wire is adapted to exit through an upwardly directed aperture in the blunt end section of the hollow stem, after passing through the second leg of the Y-shaped extension and the inner channel of the hollow stem.

The endotracheal tube of the present invention comprises a tubular member, preferably formed of a plastic material such as polyethylene or the like. The endotracheal tube includes a distal end portion incorporating a main, large diameter, beveled opening for the passage of gas, a conventional Murphy's eye, and a third, smaller diameter, slightly hooked opening, exiting from a tapered conical point disposed beneath the main beveled opening, for accepting a guide-wire therethrough.

A retrograde endotracheal intubation procedure, in accordance with the present invention, is set forth below:

After swabbing the neck of the patient to be intubated with an antiseptic solution and/or, depending on the urgency of the procedure and the condition of the patient, infiltrating a local anesthetic such as 1% xylocaine or the like proximate the proposed needle puncture site, the cricothyroid membrane or cricoid plate is localized and the hollow needle of the tracheal puncture device is inserted into the trachea through the skin, subcutaneous tissue and anterior tracheal tissues. When the hollow needle encounters the skin, with the lever actuated locking mechanism manually depressed against the upwardly directed bias of the second biasing spring, the blunt end section of the hollow stem is forced into the hollow needle by the resistance of the underlying tissue, thereby compressing the first biasing spring and exposing the sharp edges of the needle to facilitate needle puncture. As the needle enters the intratracheal space, the resistance against the first biasing spring is reduced and the hollow stem is forced outward, again protruding past the sharp edges of the needle. Substantially simultaneously thereafter, in response to the sudden reduction of resistance, the lever actuated locking mechanism is manually released. Upon release, the cantilevered arm is forced downward by the second biasing spring, and engages a detent on the hollow stem, thereby securing the blunt end of the hollow stem beyond the sharp edges of the needle. With the tracheal puncture device properly positioned within the trachea, the guide-wire is advanced through the Y-shaped plastic extension, through the inner channel of the hollow stem, and out through the upwardly directed aperture in the blunt end section of the hollow stem. Thereafter, as known in the art, the guide-wire is passed upwards through the trachea and out the mouth or nose of the patient. If the wire inadvertently passes out the nose when intubation through the mouth is desired, a hook, formed of wire, plastic or other suitable material, may be placed in the mouth to engage and pull the guide-wire out through the mouth. To insure that a sufficient length of the guide-wire has been drawn out from the mouth or nose, the guide-wire may be color coded or may include other length indicating indicia thereon.

The guide-wire is subsequently passed through the endotracheal tube of the present invention after being introduced into the small guide-wire hole in the tapered conical point thereof. After retrieving the guide-wire from the opposing end of the endotracheal tube, the guide-wire is suitably clamped in place against an upper portion of the endotracheal tube, and the guide-wire is withdrawn through the tracheal puncture needle as the attached endotracheal tube is advanced into and through the mouth or nose, past the epiglottis, through the vocal cords, and into the trachea of the patient. Finally, after the endotracheal tube reaches the needle puncture site, the guide-wire is unclamped and removed from the patient through the tracheal puncture device and/or through the top of the endotracheal tube, and the endotracheal tube is secured within the trachea in a suitable manner.

BRIEF DESCRIPTION OF THE DRAWINGS

These and other features of the present invention will become readily apparent upon reading the following detailed description and upon reference to the drawings in which:

FIG. 1 provides a cross-sectional view of a tracheal puncture device in accordance with the present invention, with the enclosed, movable, hollow stem in a retracted position as the needle penetrates the skin and tracheal tissue of a patient;

FIG. 2 is a cross-sectional view of the tracheal puncture device of FIG. 1, with the blunt end section of the hollow stem locked in position slightly beyond the sharp edges of the needle;

FIG. 3 is an enlarged view of the blunt end section of the hollow stem of the tracheal puncture device;

FIG. 4 illustrates a guide-wire carrier/aspirating syringe arrangement in accordance with the present invention;

FIG. 5 is an exploded view of the relationship between the tracheal puncture device and the guide-wire carrier/aspirating syringe arrangement.

FIG. 6 illustrates an improved endotracheal tube in accordance with the present invention;

FIG. 7 is an enlarged view of the distal end portion of the endotracheal tube illustrated in FIG. 6;

FIG. 8 illustrates a retrograde endotracheal intubation kit in accordance with the present invention.

DETAILED DESCRIPTION OF THE INVENTION

Figure 9:
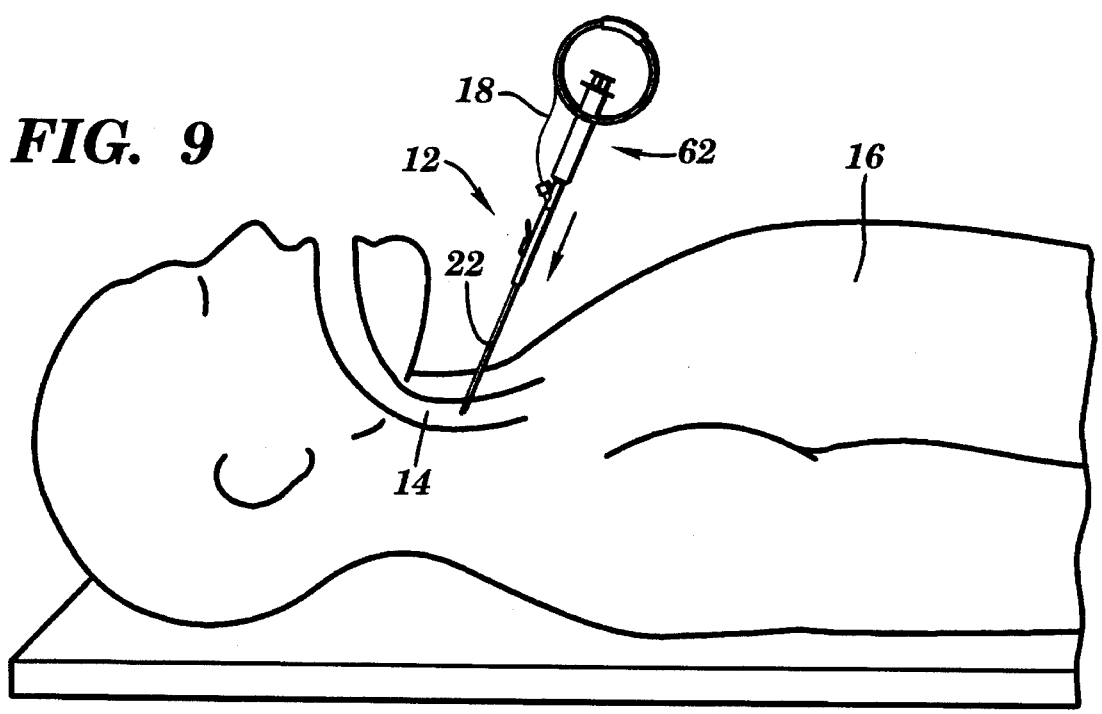
FIGS. 9 through 12 illustrate a retrograde endotracheal intubation procedure.

Referring now specifically to the drawings, there is illustrated a retrograde endotracheal intubation kit, generally designated as 10, in accordance with the present invention, wherein like reference numerals refer to like elements throughout the drawings.

As illustrated throughout the drawings, and especially in FIGS. 1 through 3, the retrograde endotracheal intubation kit 10 includes a tracheal puncture device 12 for puncturing the trachea 14 of a patient 16 prior to the passage of a retrograde intubation guide-wire 18 therethrough, wherein the guide-wire 18 preferably has a length of between about 30 to 50 inches and a diameter of between about 0.020 and 0.035 inches.

The tracheal puncture device 12 incorporates a needle hub 20 and a hollow needle 22. The hollow needle is preferably an 18 gauge needle, although needles having gauges of between about 14 to 20 may be utilized in the practice of the present invention, depending upon the diameter and/or other characteristics of the guide-wire 18. The hollow needle 22 encloses a displaceable, hollow stem 24 containing a longitudinally extending inner channel 26 therein for receiving the guide-wire 18. The hollow stem 24 further comprises a first, apertured blunt end section 28, preferably formed of a smooth plastic material or the like, and a second, opposing end section 32, slidably disposed within a guide channel 34 in the needle hub 20. To reduce injuries after an initial penetration of the trachea 14, the first, apertured blunt end section 28 of the hollow stem 24 is designed to movably protrude past the sharp edges of the needle point 30.

The needle hub 20 includes a posterior opening 36 for providing external access to the inner channel 26 of the hollow stem 24. The diameter of the posterior opening 36 is less than the diameter of end section 32 of the hollow stem, thereby limiting the rearwardly directed displacement of the hollow stem within the needle hub 20. A first biasing spring 38 is provided to continuously bias the blunt end section 28 of the hollow stem toward the needle point 30.

A spring biased, lever actuated locking mechanism 40 is utilized to lock the blunt end section 28 of the hollow stem in a position slightly beyond the sharp edges of the needle point 30, thereby preventing a needle puncture. More specifically, the lever actuated locking mechanism includes a second biasing spring 42 for upwardly biasing a manually operable lever 44, and a downwardly extending cantilevered arm 46, pivotally secured to an end portion of the lever 44 at pivot point 48, for engaging a detent 50, formed by first and second complementary stop members 52 and 54, respectively, on the hollow stem 24. When the manually operable lever 44 is depressed, the second biasing spring 42 is compressed and the bottommost section of the cantilevered arm 46 is removed from detent 50, thereby allowing the hollow stem 24 to be longitudinally displaced within the hollow needle 22. Initially, in response to the manual depression of the lever 44, and prior to the needle penetration of the skin 56, subcutaneous tissue 58 and trachea 14 of a patient, the blunt end section 28 of the hollow stem is forced beyond the sharp edges of the needle point 30 by the first biasing spring 38. As illustrated in FIG. 1, upon contact with the skin 56 and during needle penetration, the hollow stem 24 is driven into the hollow needle by the resistance of the underlying tissue, thereby compressing the first biasing spring 38 and exposing the sharp edges of the needle point 30.

Subsequent to the successful penetration of the trachea 14, the resistance against the first biasing spring 38 is removed, resulting in the spring actuated forward displacement of the hollow stem 24. In response to the reduction of resistance, the lever 44 is manually released, and the cantilevered arm 46 is forced downward against the top surface of the first stop member 52 by the downwardly directed bias of the second biasing spring 42, eventually engaging the detent 50 formed by the first and second stop members 52, 54, and securing the blunt end section 28 of the hollow stem slightly beyond the sharp edges of the needle point 30. Alternately, the lever 44 may be released as the needle penetrates into the patient, thereby forcing the cantilevered arm 46 against the top surface of the first stop member 52. Initially, the cantilevered arm is prevented from engaging the detent 50 by the penetrating resistance against the blunt end section 28 of the hollow stem; the detent is rearwardly displaced within the needle hub 20. Upon successful tracheal penetration, the penetrating resistance is eliminated, resulting in a forward, spring actuated displacement of the detent 50. When the detent is suitably positioned beneath the cantilevered arm 46, the upwardly directed bias of the second biasing spring 42 forces the cantilevered arm into a locking engagement with the detent. If desired, to facilitate the above-described detent engagement, the bottommost section of the cantilevered arm 46 may be rounded and/or the outer periphery of the opposing faces of the stop members may be downwardly beveled toward the detent.

During a retrograde endotracheal intubation procedure, as indicated in FIGS. 2 and 3, the guide-wire 18 exits through the apertured blunt end section 28 of the hollow stem 24 after passing through the posterior opening 36 in the needle hub 20 and the inner channel 26 of the hollow stem. To facilitate the upward passage of the guide-wire 18 through the trachea of a patient, the blunt end section 28 of the hollow stem incorporates an upwardly beveled aperture 60 therein.

Referring now to FIGS. 4 and 5, there is illustrated a novel guide-wire carrier/aspirating syringe arrangement 62 which is removably securable to the needle hub 20 of the tracheal puncture device 12 via a connecting port 64 (see FIGS. 1 or 2). More specifically, the guide-wire carrier/aspirating syringe arrangement includes a 5 to 10 cc aspirating syringe 66 for confirming a successful tracheal puncture, a hollow Y-shaped plastic extension 68, and a plastic wire carrier 70, for storing a length of the guide-wire 18.

The hollow Y-shaped plastic extension 66 includes a base portion 72 for insertion into the connecting port 64 of the needle hub 20, a first leg 74 for removably receiving the hub 76 of the aspirating syringe 66, and a second leg 78, incorporating a perforated gasket or seal 80, for receiving the guide-wire 18 therethrough.

The wire carrier 70 of the present invention includes an opening 82 for the withdrawal of the guide-wire 18 stored therein. The wire carrier may be fixedly secured to the barrel 84 of the aspirating syringe 66 with an appropriate adhesive or the like, or may be formed integrally therewith. Preferably, the wire carrier is formed in a substantially circular or oval configuration to allow for the unrestricted withdrawal of the guide-wire. Advantageously, the rearmost portion of the wire carrier 70 has been specifically designed and positioned to receive the palm of an operator's hand during the initial stages of a retrograde endotracheal intubation procedure, thereby synergistically providing the operational combination of the tracheal puncture device 12 and the guide-wire carrier/aspirating syringe arrangement 62 with an additional degree of support and control during tracheal penetration and the subsequent passage of the guide-wire 18 upwards through the trachea 14.

Referring now specifically to FIGS. 6 and 7, there is illustrated an endotracheal tube 86 in accordance with the present invention. As with conventional endotracheal tubes, the endotracheal tube 86 comprises a tubular body portion 88 for insertion into the trachea of a patient, an inflatable bladder 90 and associated pumping system 92 for securing the tube within the trachea and for sealing the trachea so that gas flow is confined within the endotracheal tube, a main beveled end hole 94 for the passage of gas, and a "Murphy's eye" 96 disposed on the side wall of the tube. Unlike prior art endotracheal tubes, however, the distal end portion of the endotracheal tube 86 includes a tapered, substantially conical point 98 having a supplemental guide-wire opening 100 therethrough for receiving the guide-wire 18 during a retrograde endotracheal intubation procedure. The guide-wire opening 100 is disposed beneath the main beveled end hole 94, and has a diameter slightly larger than the guide-wire 18, thereby eliminating the substantially uncontrollable and potentially injurious tube movement commonly experienced when a retrograde intubation procedure is performed using a conventional endotracheal tube.

The retrograde endotracheal intubation kit 10 is illustrated in FIG. 8. More specifically, the kit 10 includes the above-described tracheal puncture device 12, guide-wire carrier/aspirating syringe arrangement 62 and endotracheal tube 86. Preferably, the kit 10 further includes a J-shaped hook 102 for ensnaring the guide-wire 18 as it passes upwards through the trachea of a patient, a disposable clamp 104 for clamping the guide-wire 18 in place against an upper portion of the endotracheal tube 86, and a packet 106 of antiseptic wipes for cleansing the neck of the patient prior to the insertion of the tracheal puncture device therein. The kit 10 may additionally provide a pair of sterile gloves 108, a container of local anesthesia 110 and a corresponding 5 to 10 cc syringe 112 for anesthetizing the tracheal puncture site, a 5 to 10 cc syringe 114 for inflating the endotracheal tube bladder 90, and a tube stop 116 for securing the endotracheal tube 86 in position within the trachea of the patient. Finally, a tube of lubricating jelly 118 may be provided to facilitate the insertion of the endotracheal tube 86. The kit 10 is preferably sterilized and packaged in a sterile container 120 in a manner known in the art.

FIGS. 9 through 12 illustrate a retrograde endotracheal intubation procedure in accordance with the present invention.

Figure 10:
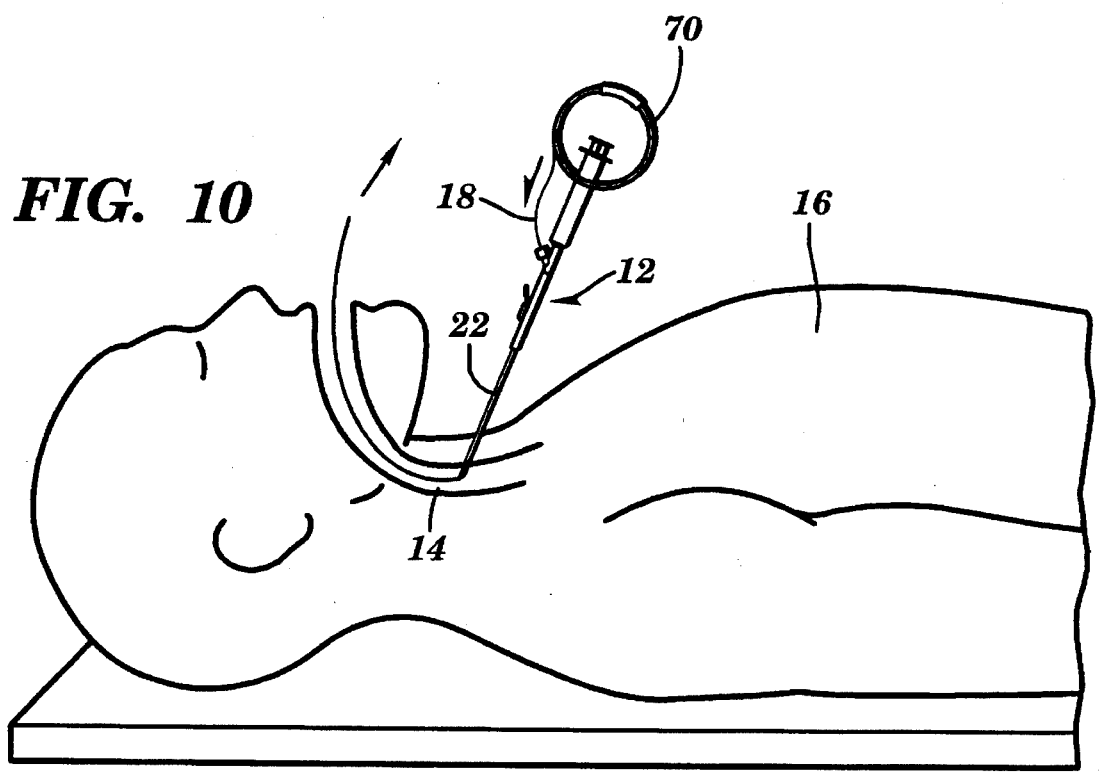
Figure 11:
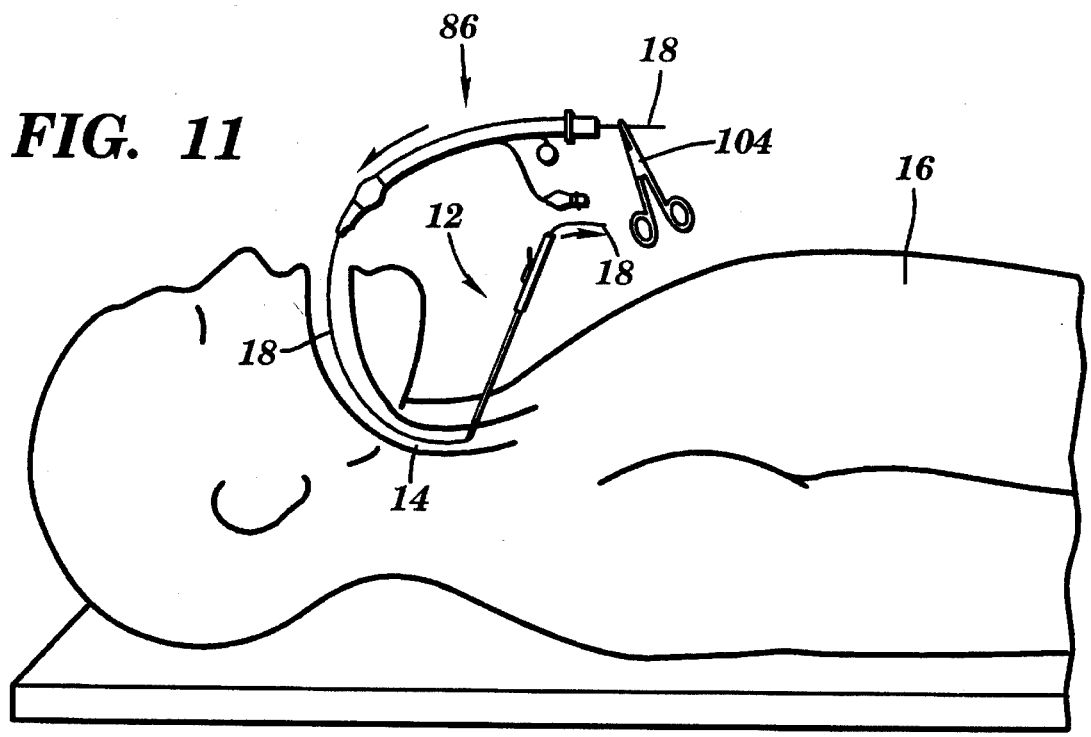
Figure 12:
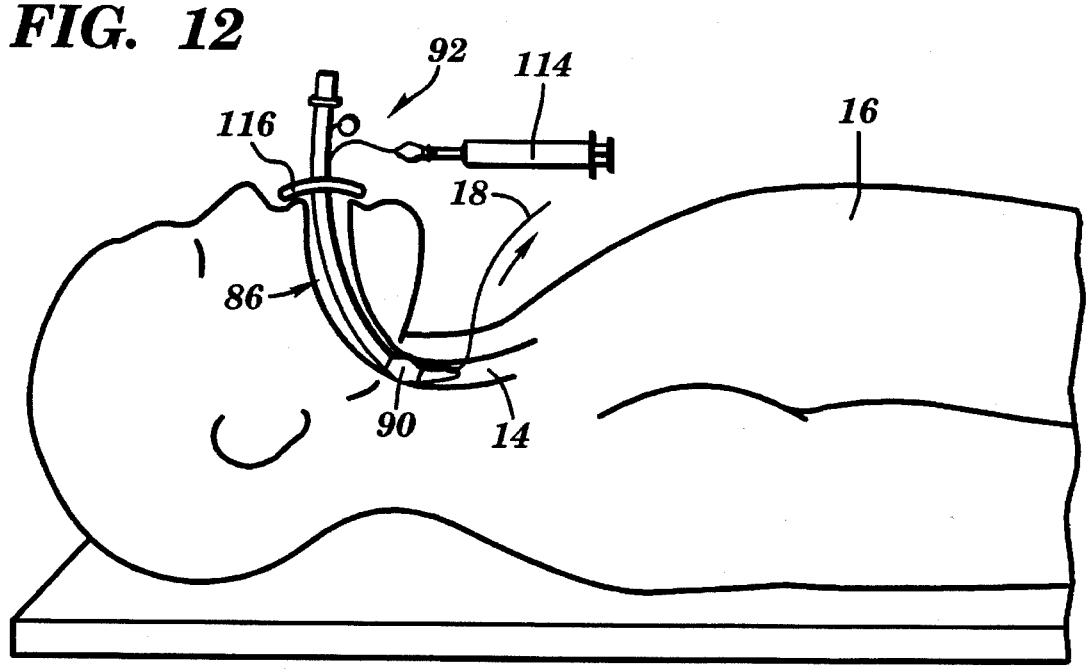

After swabbing the proposed needle puncture site on the patient 16 with an antiseptic wipe 106, and/or injecting local anesthesia 110 therein using syringe 112, the hollow needle 22 of the tracheal puncture device 12 is inserted into the trachea 14 (FIG. 9). With the tracheal puncture device 12 properly positioned within the trachea 14, the guide-wire 18 is withdrawn from wire carrier 70 and passed through the inner channel of the tracheal puncture device 12 into the trachea 14, finally exiting through the mouth of the patient (FIG. 10). The guide-wire 18 is subsequently passed through the endotracheal tube 86 after being introduced therein through the guide-wire opening 100. Thereafter, the guide-wire 18 is secured in place against an upper portion of the endotracheal tube 86 using the disposable clamp 104, and the endotracheal tube is directed into the trachea 14 as the guide-wire is withdrawn through the tracheal puncture device 12 (FIG. 11). Finally, after the endotracheal tube 86 reaches the needle puncture site, the guide-wire 18 is unclamped and suitably removed from the patient, the endotracheal tube is secured within the trachea 14 using tube stop 116, and bladder 90 is inflated through pumping system 92 with syringe 114 (FIG. 12).

The foregoing description of the preferred embodiments of the invention has been presented for purposes of illustration and description. It is not intended to be exhaustive or to limit the invention to the precise form disclosed, and obviously many modifications and variations are possible in light of the above teaching. Such modifications and variations that may be apparent to a person skilled in the art are intended to be included within the scope of this invention as defined by the accompanying claims.

We claim:

1. A retrograde endotracheal intubation kit comprising:

an elongate endotracheal tube having a length sufficient to extend from a patient's mouth into a trachea;

a tracheal puncture device having a hollow needle for providing external tracheal access;

a length of guide-wire having a first end, a second end, and a length sufficient to extend said first end through said hollow needle of said tracheal puncture device and said endotracheal tube;

a wire carrier for said guide-wire;

a clamp for securing said first end of said guide-wire to said endotracheal tube;

antiseptic; and a hook member for ensnaring said guide-wire.

2. The retrograde endotracheal intubation kit in accordance with claim 1, wherein said endotracheal tube includes:

an end portion having at least two openings, said end portion including a first beveled opening for the passage of gas, and a tapered, substantially conical projection, disposed adjacent and beneath said first beveled opening, having a second opening therein, wherein said second opening is adapted to receive said guide-wire therethrough during a retrograde endotracheal intubation procedure.

3. The retrograde endotracheal intubation kit in accordance with claim 1 further including:

an aspirating syringe; and a hollow connector for securing said aspirating syringe to said tracheal puncture device and for directing said guide-wire from said wire carrier into said tracheal puncture device.

4. The retrograde endotracheal intubation kit in accordance with claim 6 wherein the wire carrier for said guide-wire is fixedly coupled to said aspirating syringe.

5. A retrograde endotracheal intubation kit comprising:

an endotracheal tube;

a tracheal puncture device for providing external tracheal access;

a length of guide-wire for insertion through said tracheal puncture device and said endotracheal tube;

a wire carrier for said guide-wire;

a clamp for securing said guide-wire to said endotracheal tube;

antiseptic; and a hook member for ensnaring said guide-wire, wherein said tracheal puncture device includes;

a hollow needle having a distal needle point, said hollow needle enclosing a movable, hollow stem having a longitudinally extending inner channel therein and an apertured, substantially blunt end section which is adapted to movably protrude beyond said distal needle point; and a mechanism for securing the blunt end section of said movable, hollow stem beyond said distal needle point.

6. The retrograde endotracheal intubation kit in accordance with claim 5 wherein said securing mechanism includes a first catch element which is adapted to engage a second, complementary catch element on the movable, hollow stem of said hollow needle.

7. The retrograde endotracheal intubation kit in accordance with claim 6, wherein said securing mechanism includes a biasing system for continuously biasing said first and second catch elements toward an engaged relationship.

8. A retrograde endotracheal intubation kit comprising:

an endotracheal tube, said endotracheal tube including an end portion having at least two openings, said end portion including a first beveled opening for the passage of gas, and a tapered, substantially conical projection, disposed adjacent and beneath said first beveled opening and having a second opening therein, for receiving a guide-wire therethrough during a retrograde endotracheal intubation procedure; and a tracheal puncture device for providing external tracheal access during said retrograde endotracheal intubation procedure, said tracheal puncture device including a hollow needle having a distal needle point, said hollow needle enclosing a movable, hollow stem having a longitudinally extending inner channel therein and an apertured, substantially blunt end section which is adapted to movably protrude beyond said distal needle point, said tracheal puncture device further including a mechanism for securing the blunt end section of said movable, hollow stem beyond said distal needle point.

9. A retrograde endotracheal intubation kit comprising:

an endotracheal tube, said endotracheal tube including an end portion having at least two openings, said end portion including a first beveled opening for the passage of gas, and a tapered, substantially conical projection, disposed adjacent and beneath said first beveled opening and having a second opening therein, for receiving a guide-wire therethrough during a retrograde endotracheal intubation procedure; and a tracheal puncture device for providing external tracheal access during said retrograde endotracheal intubation procedure, said tracheal puncture device including a hollow needle having a distal needle point, said hollow needle enclosing a movable, hollow stem having a longitudinally extending inner channel therein and an apertured, substantially blunt end section which is adapted to movably protrude beyond said distal needle point, said tracheal puncture device further including a mechanism for securing the blunt end section of said movable, hollow stem beyond said distal needle point, wherein said securing mechanism includes a first catch element which is adapted to engage a second, complementary catch element on the movable, hollow stem of said hollow needle.

10. The retrograde endotracheal intubation kit in accordance with claim 9 wherein said securing mechanism includes a biasing system for continuously biasing said first and second catch elements toward an engaged relationship.

* * * * *